United States Patent [19]
Jackson

[11] Patent Number: 6,059,786
[45] Date of Patent: May 9, 2000

[54] SET SCREW FOR MEDICAL IMPLANTS

[76] Inventor: Roger P. Jackson, 4706 W. 86th St., Prairie Village, Kans. 66207

[21] Appl. No.: 09/177,460

[22] Filed: Oct. 22, 1998

[51] Int. Cl.[7] .................................................. A61B 17/56
[52] U.S. Cl. ............................................. 606/73; 606/61
[58] Field of Search .................................. 606/61, 65, 69, 606/73, 71

[56] References Cited

U.S. PATENT DOCUMENTS

| | | |
|---|---|---|
| D. 200,217 | 2/1965 | Curtiss . |
| 791,548 | 6/1905 | Fischer . |
| 2,201,087 | 5/1940 | Hallowell . |
| 2,239,352 | 4/1941 | Cherry . |
| 2,295,314 | 9/1942 | Whitney . |
| 2,532,815 | 12/1950 | Kindsvatter . |
| 2,553,337 | 5/1951 | Shafer . |
| 2,778,265 | 1/1957 | Brown . |
| 2,877,681 | 3/1959 | Brown . |
| 2,927,332 | 3/1960 | Moore . |
| 3,143,029 | 8/1964 | Brown . |
| 3,370,341 | 2/1968 | Allsop . |
| 3,498,174 | 3/1970 | Schuster et al. . |
| 3,584,667 | 6/1971 | Reiland . |
| 3,812,757 | 5/1974 | Reiland . |
| 3,963,322 | 6/1976 | Cryctko . |
| 4,269,246 | 5/1981 | Larson et al. . |
| 4,492,500 | 1/1985 | Ewing . |
| 4,506,917 | 3/1985 | Hansen Arne . |
| 4,641,636 | 2/1987 | Cotrel . |
| 4,763,644 | 8/1988 | Webb . |
| 4,764,068 | 8/1988 | Crispell . |
| 4,790,297 | 12/1988 | Luque . |
| 4,815,453 | 3/1989 | Cotrel . |
| 4,838,264 | 6/1989 | Bremer et al. . |
| 5,005,562 | 4/1991 | Cotrel . |
| 5,067,955 | 11/1991 | Cotrel . |
| 5,073,074 | 12/1991 | Corrigan et al. . |
| 5,129,388 | 7/1992 | Vignaud et al. . |

(List continued on next page.)

FOREIGN PATENT DOCUMENTS

| | | |
|---|---|---|
| 195455 | 9/1986 | European Pat. Off. . |
| 172130 | 2/1987 | European Pat. Off. . |
| 276153 | 7/1988 | European Pat. Off. . |
| 465158 | 1/1992 | European Pat. Off. . |
| 2467312 | 4/1981 | France . |
| 3630863 | 3/1988 | Germany . |
| 373809 | 5/1989 | Germany . |
| 203508 | 9/1923 | United Kingdom . |
| PCT92/03100 | 3/1992 | WIPO . |
| PCT94/10927 | 5/1994 | WIPO . |
| PCT94/10944 | 5/1994 | WIPO . |
| PCT96/06576 | 3/1996 | WIPO . |

OTHER PUBLICATIONS

Two Drawings of Sofamor dated Mar. 10, 1994 and Sep. 20, 1994.

*Primary Examiner*—Michael Buiz
*Assistant Examiner*—Daphna Shai
*Attorney, Agent, or Firm*—Litman, Kraai & Brown, L.L.C.; John C. McMahon

[57] ABSTRACT

A low profile and removable set screw for use in connecting one medical implant to another and for similar uses. The set screw has a base and a head that is breakable from the base in a breakaway region at a preselected torque, such that the head allows rotation of the screw and torquing of a tip of the base against one of the implants during installation. The screw includes a groove or notch at the breakaway region to trigger breaking. The screw also includes a pair of slots extending radially from an outer threaded surface of the base part way into the base. The slots intersect with the breakaway region, but not with each other leaving a center core in the base. A tool is provided for removing the base after the head is broken away. The tool includes a pair of spaced ears that are received in the slots and provide for rotation of the base by rotating the tool. A bore of larger width than the slots is centered on each slot at the breakaway region providing relief for metal adjacent to the bores during torquing and breaking.

19 Claims, 2 Drawing Sheets

U.S. PATENT DOCUMENTS

| | | |
|---|---|---|
| 5,147,360 | 9/1992 | Dubousset . |
| 5,154,719 | 10/1992 | Cotrel . |
| 5,261,907 | 11/1993 | Vignaud et al. . |
| 5,261,912 | 11/1993 | Frigg . |
| 5,282,707 | 2/1994 | Palm . |
| 5,312,404 | 5/1994 | Asher et al. . |
| 5,346,493 | 9/1994 | Stahurski et al. . |
| 5,364,400 | 11/1994 | Rego, Jr. et al. . |
| 5,382,248 | 1/1995 | Jacobson et al. . |
| 5,385,583 | 1/1995 | Cotrel . |
| 5,487,742 | 1/1996 | Cotrel . |
| 5,496,321 | 3/1996 | Puno et al. . |
| 5,499,892 | 3/1996 | Reed . |
| 5,507,747 | 4/1996 | Yuan et al. . |
| 5,562,663 | 10/1996 | Wisnewski et al. . |
| 5,630,817 | 5/1997 | Rokegem et al. . |
| 5,643,260 | 7/1997 | Doherty . |
| 5,653,710 | 8/1997 | Härle . |
| 5,697,929 | 12/1997 | Mellinger . |

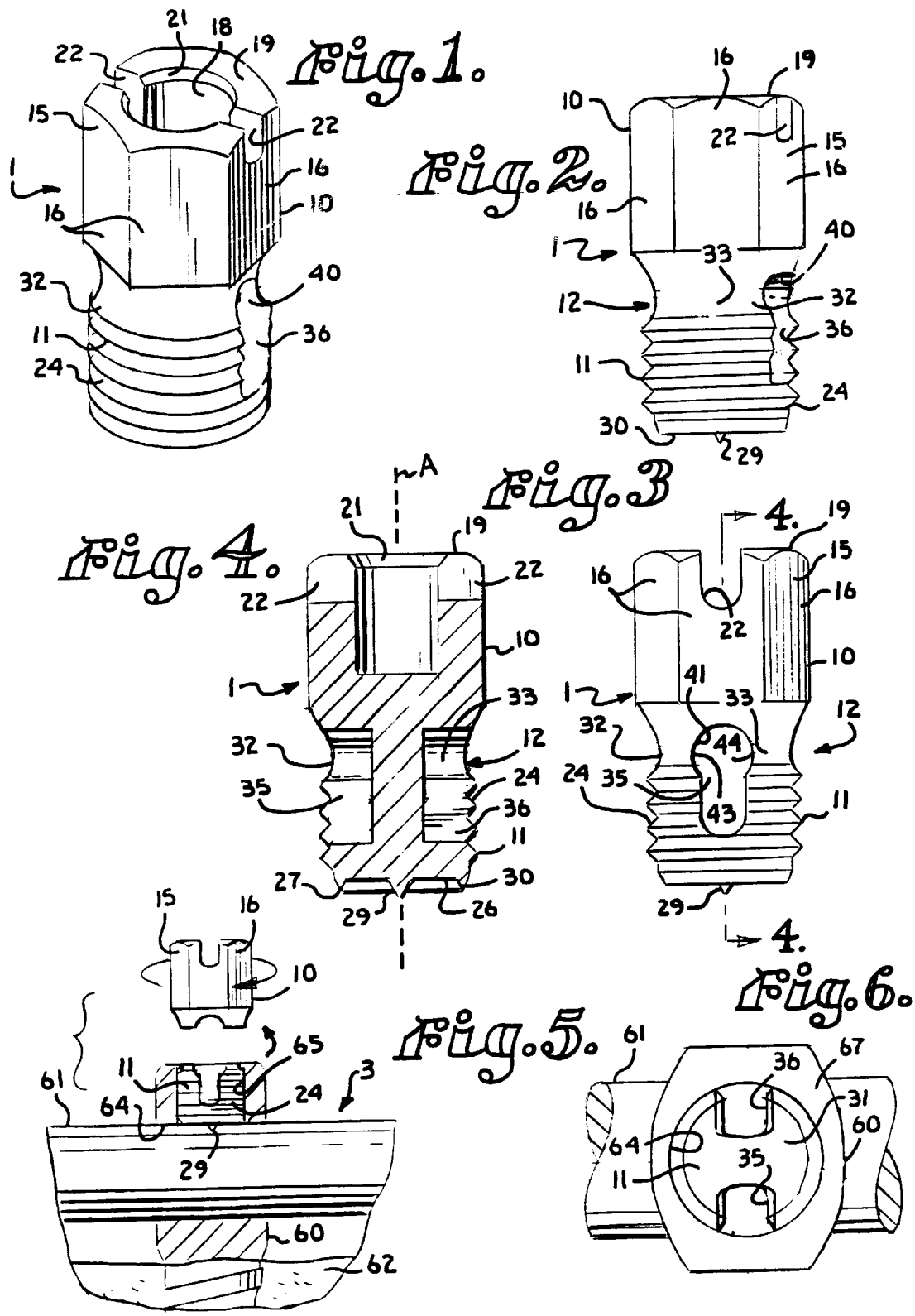

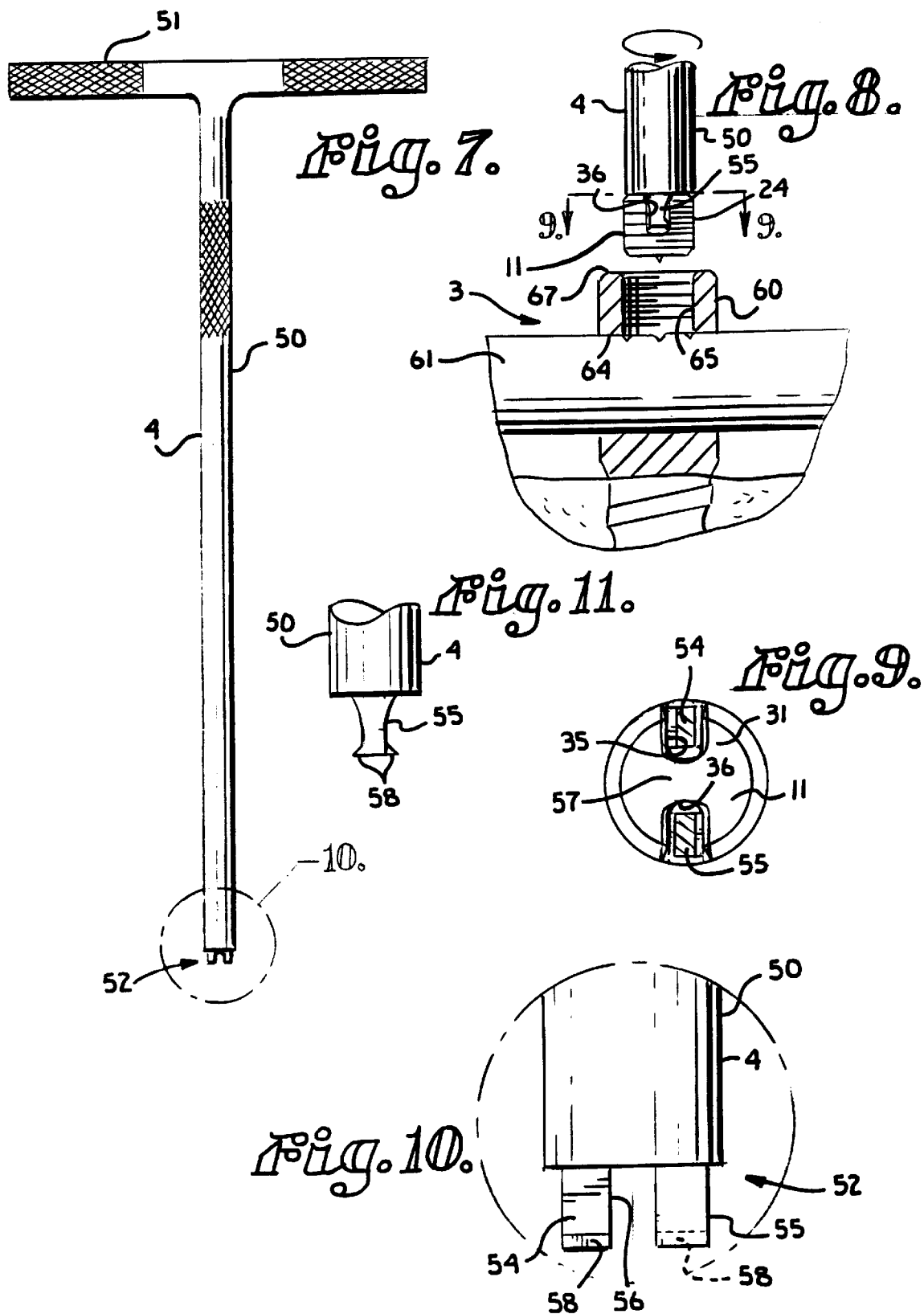

SET SCREW FOR MEDICAL IMPLANTS

BACKGROUND OF THE INVENTION

The present application is directed to a set screw for use in applications where it is important for the head of the set screw to break away to leave a clean profile, but for the set screw to be removable, especially set screws for use in conjunction with medical implants.

Over recent years, medical implants for support of and correction of defects in various portions of the body, especially the spine, have improved dramatically. It is desirable to continue to improve these implants, so that the implants provide greater strength and durability and so that the implants are effective for the life of the patient. Furthermore, it is very desirable to provide such an implant which is low profile and interferes as little as possible with tissues surrounding the implant. Because the set screw which holds together various parts of the implant, especially spinal implants, has often been a limiting factor with respect to such implants, current attention has been directed to improving the set screw.

Set screws of the type used in medical implants have among other problems two somewhat conflicting requirements. It is important to be able to grasp the set screw and apply rotational force to it until it is torqued to a particular preselected amount. Because the torque applied to such set screws is comparatively high, this normally requires a protruding head with an external surface which can be grasped by a driving tool to set the screw at the preselected torque.

On the other hand, if the head sticks outwardly from the set screw after installation, then this presents a problem, since the head will interfere with surrounding tissue, such as muscle, ligament and the like. Consequently, set screws have been developed recently that have a break off head that is designed to break away from a base of the set screw upon the application of the preselect torque.

While the break away head satisfies the two above and noted requirements, it presents a problem of its own. That is, once the head breaks away, it is then quite difficult to grasp the remaining set screw base to remove it, should the implant need to be adjusted during installation or should later work on the implant require removal of the set screw.

Therefore, there needs to be some mechanism provided to allow the set screw to be removed. While the force or torque required to remove the base of the set screw after it has been installed is less than the installation torque, it is normally only approximately 70% of that required to install the set screw. Thus, a relatively large torque must be applied to the set screw base to remove it. Because it is imbedded in the implant and because it is low profile, there is little surface to grasp to allow the surgeon to remove the set screw, once installed.

Applicant, in a manner described in prior patent applications of applicant, and others have tried to develop different ways to effectively remove the set screw base once it has been broken away from the driving head. One of applicant's prior concepts was to provide an internal bore in the base of the set screw which may be a smooth wall bore or which may include some structure for assisting in the gripping of the wall by a tool and then utilizing a easy out tool or the like to try to grasp the interior of the bore for removal. Such structure was designed to try to provide sufficient torque to remove the base and in some cases functioned satisfactorily for this purpose, but in other cases did not. Because of the high torque applied to the base, it is not an easy process to remove the screw in this manner. In addition, the leverage radius that can be used on the interior wall is substantially less than can be applied to the exterior wall of the set screw.

Consequently, applicant foresaw a need for a set screw that would have a break away head to allow a preselected torque to be applied to the set screw and then have the head break away leaving a lower section and further that provided the surgeon with structure near the radial exterior of the screw base that could be accessed by a tool that would allow the surgeon to apply removal torque to remove the set screw with substantially greater grip and with substantially greater mechanical advantage as compared to use of a tool in a central bore.

SUMMARY OF THE INVENTION

A set screw is provided that is especially suited for use in medical implants and the like wherein it is desired to have a low profile set screw preferably that is installed at a preselected torque and is then removable should removal be required. The set screw includes a threaded lower section or base and a breakoff head.

In particular, the base and the head are originally joined at a location having a partial or circumferential notch or groove in the circumference of the screw between the head and bore, such that as torque is increasingly applied to the head, the torque on the head reaches a preselected amount and the head breaks from the base at the groove generally in a plane perpendicular to an axis of rotation of the screw.

The base includes a threaded surface that is radially spaced from an axis of rotation and that is received in a similarly and matingly threaded bore in a first medical implant or the like. The bottom of the base includes an axially projecting tip that may be a point, a ring, both or another similar structure for engaging a second implant so as to secure the second implant relative to the first.

The head includes an outer grippable surface for gripping and applying torque and an internal bore to receive tools for grinding during installation.

Located along the outer wall of the screw and extending partially along the base and partially along the head are a pair of non-intersecting or spaced slots. The slots extend radially part way into the screw and are preferably positioned opposite or diagonally with respect to each other. The slots extend through the threads on the base. The slots provide for removal of the base after the set screw is installed and the head broken away.

A tool is provided to remove the base utilizing the slots. The tool includes a manipulative handle operably connected to a pair of ears adapted to be received in the base slots. The ears are spaced, sized and positioned to be received in the slots radially inward of the threads so that the tool can be inserted into the slots without engaging or interfering with the threads of the first implant bore to allow counterclockwise rotational force to be applied to the base through the ears by rotation of the tool by a user and in this way remove the base from the implants.

Also associated with the slots is a circular bore that is of slightly greater diameter than the side to side width of the slots, the bore is preferably positioned to be centered on the notch or groove along which breakage between the head and base occurs. The bore provides relief at the location of breakage. That is, normally when breakage between the head and base occur, some of the metal adjacent to the slots may be twisted into the slot opening, thereby preventing easy access of the tool to the slot. With the bore, adjacent metal that is twisted is received in the portion of the bore outside the slot, thereby allowing the tool to be easily received in the slot.

OBJECTS AND ADVANTAGES OF THE INVENTION

Therefore, the objects of the present invention are: to provide a set screw for use in conjunction with medical implants and the like wherein the set screw has a low profile after installation, provides for installation to a preselected torque and is removable from the implant after installation; to provide such a set screw having a breakoff head and a region of reduced cross-section produced by a notch or groove that is centered in a plane perpendicular to the axis of installation so as to trigger breakage at a preselected location; to provide such a set screw having axially extending and radially penetrating slots that extend along the outer surface of the screw and intersect with the location whereat the head breaks from the base, the slots being positioned and shaped to receive a tool to apply counterclockwise rotation to the base to remove the set screw from the implant; to provide such a set screw including a relief region adjacent to the slots to receive twisted metal upon breakage of the head from the base so as to allow full access of the slots to the tool; to provide such a screw that has such slots that are positioned to provide a mechanical advantage to removal of the base over that provided by mechanisms and systems that remove the base through internal structure; to provide a tool having ears adapted to be received in the slots for applying a removal torque; to provide such a tool wherein the ears include gripping cleats; to provide such a set screw in combination with medical implants to secure a first implant to a second implant; and to provide such a set screw, tool and overall implant system that is comparatively easy to use, easy to produce, and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a removable set screw with a break off head and a base in accordance with the present invention.

FIG. 2 is a front elevational view of the set screw.

FIG. 3 is a side elevational view of the set screw.

FIG. 4 is a cross sectional view of the set screw, taken along line 4—4 of FIG. 3.

FIG. 5 is a fragmentary side elevational view of the set screw on a reduced scale positioned in an implant with a head of the set screw broken away from a lower section thereof and having portions removed to show detail thereof.

FIG. 6 is an enlarged fragmentary top plan view of the set screw and implant of FIG. 5 after breakaway of the set screw head.

FIG. 7 is a side elevational view of a tool to remove the set screw base from the implant.

FIG. 8 is a fragmentary side elevational view of the implant of FIG. 5 with the set screw base being removed by the removal tool.

FIG. 9 is an enlarged and cross sectional view of the set screw base and tool, taken along line 9—9 of FIG. 8.

FIG. 10 is an enlarged fragmentary view of the removal tool, taken within circle 10 of FIG. 7.

FIG. 11 is an enlarged fragmentary front elevational view of the removal tool.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a set screw in accordance with the present invention used in conjunction with a medical implant system 3 (FIG. 5) and having an associated removal tool 4 (FIG. 7).

The set screw 1 has an upper section or head 10 and a lower section or base 11 originally joined together along a planar breakaway zone or region 12. The set screw 1 is rotatable about a central axis A that passes longitudinally through the center of the screw 1.

The head 10 has an outer grippable surface 15, which in the illustrated embodiment includes six planar faces 16 joined together in a hexagonal shape, such that the faces 16 lie in planes that are parallel to but are spaced from the axis A.

The surface 15 is sized and shaped to receive a driving or installation tool (not shown) of any conventional type for torquing or clockwise (as viewed from a top 19 of the head 10) rotating the set screw 1. A bore 18 extends from the top 19 of the head 10 partially through the head 10 and is coaxial with axis A. The bore 18 preferentially receives a nipple from a driving tool during insertion. Near the top of the bore 18 is a relief 21. A pair of tool receivers 22 and 23 extend between the bore 18 and the surface 15 near the head top 19. The receivers 22 operably receive a portion of a driving tool during installation of the set screw. A suitable driving tool for use with the set screw 1 of the present invention is illustrated in my co-pending application Ser. No. 08/726,828 on TOOLS FOR USE IN INSTALLING OSTEOSYNTHESIS APPARATUS UTILIZING SET SCREW WITH BREAK-OFF HEAD, now U.S. Pat. No. 5,941,885, which is incorporated herein by reference.

The purpose of the head 10 is to allow a surgeon or other user to apply a driving tool to grip the surface 15 and apply rotational force or torque to the screw 1. The head surface 15 allows good leverage about the axis A and mechanical advantage. As discussed in greater detail below, the head 10 breaks away from the base 11 at a preselected torque.

Although the illustrated surface 15 is hexagonal in cross section, surfaces of other shapes including non polyhedral shapes may be utilized for the grippable surface 15.

The base 11 has a radially outer surface 24 that is threaded and which is coaxial with but spaced from the axis A.

The thread of the threaded surface 24 is sized and shaped to be received in an implant as described below. A bottom 26 of the base 11 has an axially projecting tip 27 that provides frictional engagement and preferably penetration into an object against which the screw 1 is operably set. The tip 27 that extends outward parallel to the axis A. The tip 27 operably engages a structure against which the set screw 1 is set, also as described further below. The tip 27 of the illustrated embodiment includes a point 29 and sharp edged ring 30 that is radially spaced from the point 29. Although the point 29 and ring 30 are shown in the illustrated embodiment, it is foreseen that other types of projecting tips may be used in accordance with the present invention.

Located between the head 10 and base 11 is the breakaway region 12. The location 12 is in a plane that is typically perpendicular to the axis A. When the head 10 breaks from the base 11, as shown in FIG. 5, an upper surface 31 is left on the base 11. The region 12 has a reduced cross sectional area perpendicular to the axis A, as compared to the surrounding regions of the screw 1. Preferably, the breaking of the head 10 from the bore 11 leaves the base upper surface 31 relatively smooth and free from burrs, although the metal will deform slightly sideways due to twisting. The region 12 in the illustrated invention is produced by a circumferential groove 32 that has a center line 33 that lies in a plane perpendicular to the axis A. Although a circumferential uniform groove 32 is used to trigger breakage in the present embodiment, it is foreseen that other structures such as a non-uniform notch may also be used for this purpose.

Extending radially inward from the head surface 15 and the base surface 24 is a pair of spaced and non-intersecting slots 35 and 36. Each of the slots 35 and 36 is elongate with the greatest length being aligned parallel to the axis A. Each of the slots 35 and 36 is formed by milling or drilling and extends perpendicular to or radially inward toward the axis A. Each slot 35 and 36 is positioned in opposed relationship or diametrically relative to the other.

Each slot 35 and 36 extends substantially along the base outer surface 24 and in the illustrated embodiment each slot 35 and 36 extends along about two thirds of the surface 24. The slots 35 and 36 extend through the breakaway region 12 and in the illustrated embodiment extend partly along the head surface 15. The depth of each slot 35 and 36 may vary somewhat, but must accommodate the removal tool 4. In the illustrated embodiment the slots 35 and 36 each extend approximately 60% of the distance between the lowest part of the threaded surface 24 and the axis A. The width of each of the slots 35 and 36 in the illustrated embodiment is about one third of the diameter of the base 11, but it is foreseen that slots of other size may be used in accordance with the invention, especially considering the size and shape of the tool 4 and the overall diameter of the set screw 1.

Relief bores 40 and 41 are positioned to be centered over each respective slot 35 and 36 relative to the minor axes of the slots 35 and 36, as shown in FIG. 3. The bores 40 and 41 are also centered on the breakaway region 12. Each bore 40 and 41 is somewhat larger than the associated slot 35 and 36 so as to form a relief area 43 and 44 therebetween. The relief areas 43 and 44 receive deformed metal due to twisting and breaking at the breakaway region 12 to prevent such metal from entering and blocking the slots 35 and 36. The bores 43 and 44 are cylindrical and in the illustrated embodiment have the same depth as the slots 35 and 36.

The illustrated set screw removal tool 4 is T-shaped and includes an elongate shaft 50 with a handle 51 extending perpendicularly in opposite directions from one end thereof. At an end opposite the handle 51 is a set screw engaging tool head 52. As is best seen in FIGS. 10 and 11, the tool head 52 includes a pair of axially projecting and slot receiving tabs, lugs or ears 54 and 55. The ears 54 and 55 are separated or spaced by a slot or channel 56. The ears 54 and 55 are sized and shaped to be received inward of the thread and within the slots 35 and 36 once the head 10 has been broken from the base 11 and the channel 56 spans a center core 57 of the set screw 11 between the slots 35 and 36. The ears 54 and 55 adapted to be positioned or set in the slots 35 and 36, as is illustrated in FIGS. 8 and 9. The channel 56 is sufficiently large in size to receive the center core 57 of the set screw located between the slots 35 and 36. The ears 54 and 55 are also sized to not extend outwardly into the thread of either the base 11 or mating thread of the implant system 3.

Located near a lower end of each of the ears 54 and 55 is a cleat 58. The cleats 58 are positioned on the sides of the ears 54 and 55 that engage the slots 35 and 36 when the tool is rotated counterclockwise to remove the base 11. As a substantial amount of torque is applied to the tool 4 to remove set screw base 11 once it has been secured to the implant system 3, the cleats 58 serve to grip the sidewalls of the slots 35 and 36 and reduce the likelihood of slippage. If one of the ears 54 or 55 should break during removal of the base 11, the broken ear is simply removed and a new tool 4 is utilized for the purpose.

Shown in FIGS. 5, 6 and 8 is the set screw 1 in combination with the medical implant system 3. The medical implant system 3 that is illustrated includes a bone screw 60 and a rod 61. In the illustrated embodiment the bone screw 60 is implanted in a vertebral bone 62. In conventional medical implant systems of the type illustrated herein, there are a wide range of parts that are utilized including hooks, connectors, bars, plates and numerous other elements that are all interconnected together by means of set screws. The set screw 1 of the present invention may be used for interconnecting together any of the various elements.

In the illustrated embodiment, the bone screw includes a first bore 62 that is sized and shaped to slideably receive the rod 61 and is often perpendicular to the central elongate axis of the bone screw 60. The rod 61 is positioned in a first rod receiving bore 64 in the illustration. The bone screw 60 includes a second threaded bore 65 which intersects with the first bore 64 and which is generally aligned to be coaxial with the bone screw 60. The thread of the thread bore 65 is sized and shaped to receive the thread on the base outer surface 24 of the set screw 1.

The set screw 1 is, thus, first threaded into the threaded bore 65 until the projecting tip 19 engages the rod 61. Thereafter, clockwise rotation producing an increasing torque is applied to the set screw 1 to set the set screw 1 both within the threaded bore 65 and against the rod 61. As the set screw 1 is rotated, the set screw point 29 and ring 30 engage and partially penetrate into the rod 61. As increasing torque is applied to the set screw 1, the torque finally reaches a preselected torque where the head 10 breaks from the base 11, as is illustrated in FIG. 5.

The torque can be substantially varied according to the system and set screw, but has been found that a torque of 90 inch pounds is highly effective when setting the set screw so as to prevent relative motion between the various elements of the system 3, including the bone screw 60 and rod 61.

Subsequent to the head 10 breaking from the base 11, the upper surface 31 of the base 11 is preferably beneath or substantially even with a top 67 of the bone screw 63. In this manner the set screw 1 does not have a projecting head 10 and is comparatively low profile.

Consequently, in operable use, the set screw base 11 secures a first implant such as the bone screw 60 to a second implant such as the rod 61 by means of the set screw 1 being threadably held in the first implant bore 65 and set against the second implant or rod 61 by rotation and application of torque thereto.

Subsequent to the set screw base 11 being set, it is sometimes necessary to remove the base 11. This occurs when the implant system 3 must be adjusted during installation or at a later time when original parts of the system must be removed for some reason. When this occurs, the removal tool 4 is utilized. In particular, the removal tool ears 54 and 55 are placed in the slots 35 and 36. Thereafter the user applies counterclockwise rotation to the handle 51 to urge the ears 54 and 55 against respective sides of the slots 35 and 36. Sufficient torque is applied in this manner to unseat the base 11. The ears 54 and 55 are sufficiently radially inward so as not to interfere with the threads on the interior of the bone screw threaded bore 65. This allows a subsequent set screw 1 to be utilized in the bore 65 to reset the bone screw 60 relative to the rod 61.

While the torque required to unseat the set screw base 11 varies from system to system and with the type of metal used, it has been found that the torque required to unseat the base 11 is often approximately 70% of the torque required to seat the screw.

It is foreseen that the set screw 1 of the present invention can be constructed of many different types of materials. When the set screw 1 is to be utilized for medical implants, the material construction should be as compatible as possible with implantation and it has been found that stainless steel and titanium are typically preferred as materials of construction for such uses.

Although the set screw of the present invention is described and illustrated in conjunction with mainly medical implants, as it advantageously provides for many of the requirements peculiar to such implants as opposed to other types of set screws, it is foreseen that the set screw of the present invention may also be used with other types of systems.

It is to be understood that while certain forms of the present invention have been illustrated and described herein, it is not to be limited to the specific forms or arrangement of parts described and shown.

What is claimed and desired to be secured by Letters Patent is as follows:

1. A set screw for operably joining a first element to a second element comprising:
   a) a head having a surface for gripping, rotating and applying torque to said set screw;
   b) a base initially joined to said head and having a threaded surface adapted to be received into a threaded bore of the first element;
   c) said head and said base being joined at a breakaway region adapted to break upon the application of a preselected torque such that said head separates from said base; and
   d) a pair of slots that do not pass through an axial center of rotation of the set screw base; said slots being located in and extending radially inward from said base threaded surface; said slots each intersect with said breakaway region; and said slots being adapted to receive a removal tool inward of said threaded surface subsequent to said head being broken from said base to allow application of torque to said base and rotate said base counterclockwise.

2. The set screw according to claim 1 wherein:
   a) said slots are diametrically opposed and are separated by a center core.

3. The set screw according to claim 2 wherein:
   a) said slots are elongate and have a major length parallel to an axis of rotation of said set screw.

4. The set screw according to claim 1 including:
   a) a region of relief overlapping said break-away region and intersecting with at least one of said slots; said region of relief adapted to receive deformed portions of said base during setting of said base against the second element such that said deformed sections do not block access to said slots.

5. The set screw according to claim 1 further in combination with a removal tool; said removal tool comprising:
   a) an elongate shaft;
   b) an operator grip for operably rotating said shaft; and
   c) a pair of ears projecting from said shaft; said ears being sized and positioned so as to be receivable in respective slots of said base after said head is broken from said base such that removal torque may be operably applied to said base through said ears by said removal tool.

6. The combination according to claim 5 wherein:
   a) said tool ears each include a cleat adapted to engage a respective slot upon application of removal torque to reduce the likelihood of slippage of said ears.

7. A set screw according to claim 1 wherein:
   a) said slots are positioned, sized and shaped to be available for entry of a removal tool after said head is broken from said base and are not accessible by a removal tool prior to said head being broken from said base when said set screw base is located within a threaded bore.

8. A set screw according to claim 1 in combination with the first and second elements wherein:
   a) said first element is an elongate member portion of a first medical implant; and
   b) said second element is a second medical implant having a first bore for operably receiving said elongate member portion and a second threaded bore for receiving said set screw; said first and second bores intersecting.

9. The combination according to claim 8 wherein:
   a) said set screw is sized and shaped such that as said base engages and becomes set against said elongate member, said head breaks from said base such that said breakaway region is entirely within said second threaded bore and thereby low profile.

10. The combination according to claim 9 wherein:
    a) said slots are not available for entry by a tool when said set screw is in said threaded bore prior to said head breaking from said base and wherein said slots are available for entry by a removal tool after said head breaks from said base.

11. A set screw comprising:
    a) a base having a threaded surface adapted to be received in a threaded bore;
    b) a head originally joined to said base at a breakaway region located by an exterior notch; said head being shaped and configured to receive a driving tool for rotating and applying torque to said set screw; said head breaking from said set screw at a preselected torque at said breakaway region; and
    c) a removal slot that extends radially inward from said threaded surface and is adapted to receive a removal tool, when said set screw is operably received in a threaded bore; said slot being non-accessible by a removal tool when said head is joined to said base; and said slot is accessible by a removal tool after said head has broken from said base.

12. The set screw according to claim 11 wherein:
a) said slot is a first slot and including a second slot.

13. The set screw according to claim 12 wherein:
a) said first and second slots are diametrically opposed from each other and are spaced by a center core.

14. The set screw according to claim 11 wherein:
a) said slots are longer parallel to a rotational axis of said set screw than wide and open into an upper surface of said base after said head breaks from said base.

15. A medical implant system comprising:
a) a first implant having a first bore and a second threaded bore intersecting with said first bore;
b) a second implant operably received in said first implant first bore;
c) a removable set screw for operably securing said first implant to said second implant; said screw being threadably receivable in said first implant second threaded bore, abutted against said second implant and thereafter torqued to a preselected torque;
d) said set screw having:
  1) a base with an external threaded surface sized and shaped to be threadably received in said first implant threaded bore, a bottom having a tip operably sized and shaped to frictionally engage said screw implant and a top opposite said tip;
  2) a head breakably attached to said base top and adapted to receive an installation tool to drive said set screw base into said first implant threaded bore; said head breaking from said base upon the application of said preselected torque; subsequent to said head breaking from said base, said base being relatively low profile with respect to said first implant threaded bore;
  3) said base also including a pair of slots; each of said slots extending radially inward from said base threaded surface and intersecting with said base top; said slots being diametrically opposed to each other and spaced by a center core of said base; when said base is in said first implant threaded bore, said slots are often accessible to a removal tool said head is broken from said base and are non-accessible to a removal tool when said head is attached to said bore; and
  4) a break initiating notch between said head and said base.

16. The system according to claim 15 wherein:
a) said set screw includes a pair of radially extending bores in said screw; each of said bores being positioned to intersect with a respective slot and with the base top such that one of said bores operably provides relief adjacent each respective slot in association with the breaking away of said head.

17. The system according to claim 16 wherein:
a) each of said slots is elongated parallel to the axis of rotation of said base.

18. The system according to claim 17 wherein:
a) each of said bores is wider than said respective slots.

19. The system according to claim 18 wherein:
a) each of said bores is centered in a respective slot so as to extend outward on either side of a respective slot and is also centered on said notch.

* * * * *